United States Patent [19]
Bitdinger

[11] Patent Number: 5,250,037
[45] Date of Patent: Oct. 5, 1993

[54] SYRINGE HAVING NEEDLE ISOLATION FEATURES

[75] Inventor: Ralf V. Bitdinger, La Cote Herbeys, France

[73] Assignee: Becton, Dickinson and Company, Franklin Lakes, N.J.

[21] Appl. No.: 992,958

[22] Filed: Dec. 18, 1992

[51] Int. Cl.$^5$ .............................................. A61M 5/32
[52] U.S. Cl. ................... 604/192; 604/201; 604/206; 604/242; 604/411; 604/413
[58] Field of Search .............. 604/192, 263, 240–242, 604/244, 201, 200, 206, 187, 188, 218, 411–415, 232, 905; 128/919; 206/263, 264

[56] References Cited

U.S. PATENT DOCUMENTS

| | | | |
|---|---|---|---|
| 2,828,742 | 4/1958 | Ashkencz | 604/206 X |
| 3,512,524 | 5/1970 | Prewe | 206/206 X |
| 3,916,893 | 11/1975 | DeFelice | 604/206 |
| 4,178,930 | 12/1979 | Fisher | 604/201 X |
| 4,639,250 | 1/1987 | Rycroft | 604/201 |
| 4,740,205 | 4/1988 | Seltzer et al. | 604/192 |
| 4,758,230 | 7/1988 | Rycroft | 604/118 |
| 4,865,592 | 9/1989 | Rycroft | 604/197 |
| 4,932,940 | 6/1990 | Walker et al. | 604/110 |
| 5,190,521 | 3/1993 | Hubbard et al. | 604/51 |

FOREIGN PATENT DOCUMENTS

| | | | |
|---|---|---|---|
| 1191634 | 5/1970 | United Kingdom | 604/242 |

Primary Examiner—John D. Yasko
Assistant Examiner—Mark O. Polutta
Attorney, Agent, or Firm—John L. Voellmicke

[57] ABSTRACT

A hypodermic syringe has a syringe barrel with a distal end and a passage therethrough communicating with a fluid-receiving chamber in the syringe barrel. A barrier extends across the passage to isolate the fluid in the chamber. A needle cannula is mounted to a needle hub slidingly engaged at the distal end of the syringe barrel. The needle cannula includes a proximally facing point for piercing the barrier in the passage to the chamber of the syringe barrel. A needle shield is mounted to the distal end of the syringe barrel, and cam means are provided for cam-guided rotational movement between the needle shield and the syringe barrel. The cam shape causes the needle shield and the needle cannula to move proximally for initially piercing the barrier and then to move distally to enable separation of the needle shield.

19 Claims, 7 Drawing Sheets

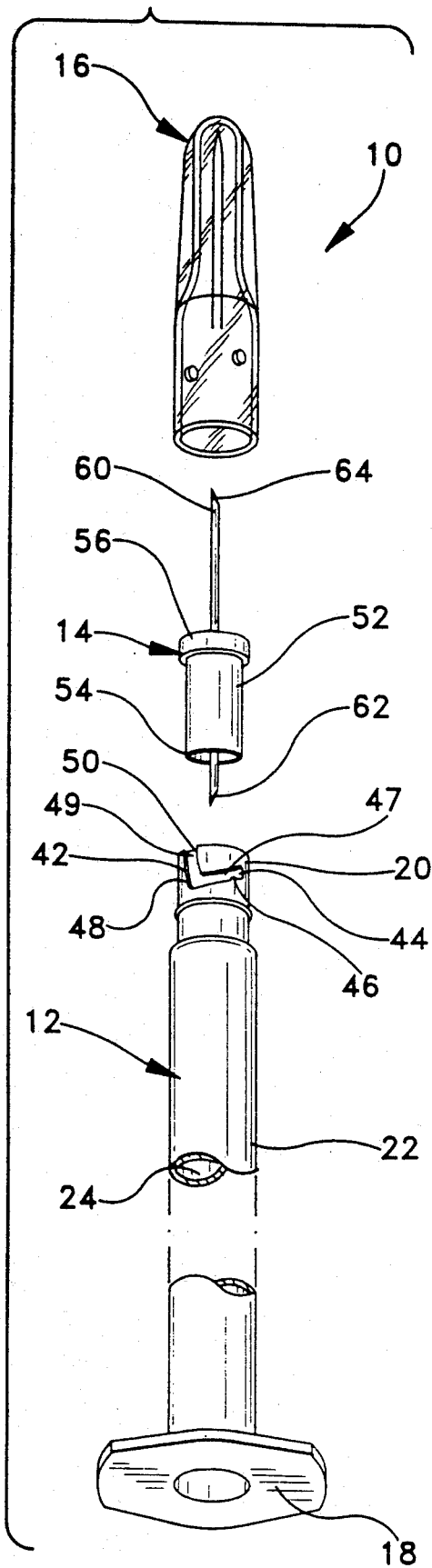
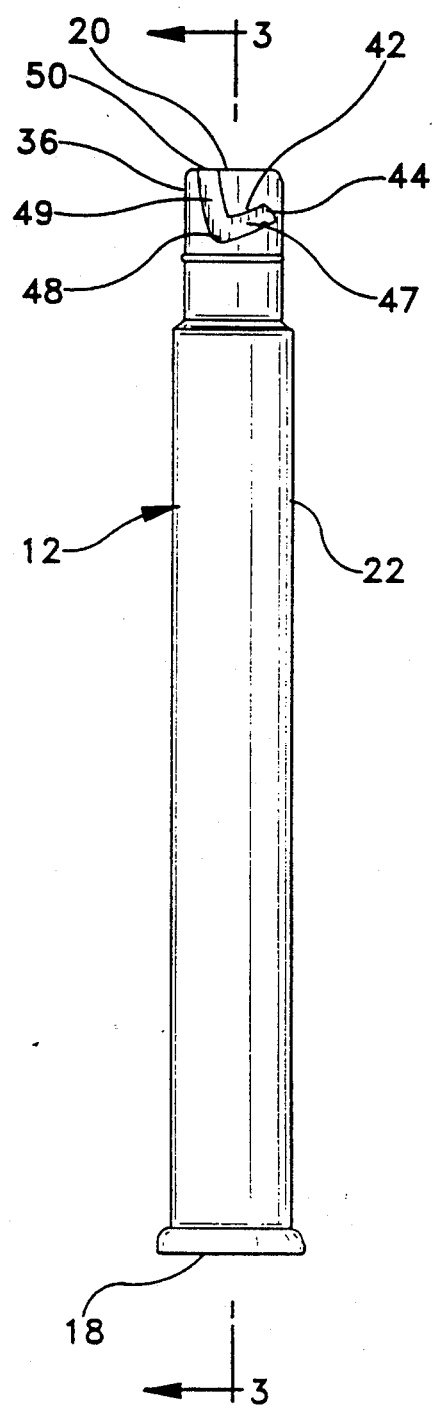

SYRINGE HAVING NEEDLE ISOLATION FEATURES

BACKGROUND OF THE INVENTION

1. Field of the Invention

The subject invention relates to a hypodermic syringe having activation structures which enables an initial piercing of a barrier in the syringe and subsequent removal of a needle shield in response to a continuous motion of the activation assembly.

2. Description of the Prior Art

A hypodermic syringe has a syringe barrel with an open proximal end and an opposed distal end. A cylindrical wall extends between the ends of the barrel to define a fluid-receiving chamber. The distal end of the syringe barrel includes a passage for fluid communication with the chamber. A needle cannula may be mounted to the distal end of the barrel and a needle shield may be removably mounted over the needle cannula to protect the needle before use. The hypodermic syringe also has a plunger in sliding fluid-tight engagement with the cylindrical wall of the chamber. Movement of the plunger toward the distal end of the syringe barrel urges fluid in the chamber toward the needle cannula.

Many hypodermic syringes are pre-filled with a fluid that must be isolated in the syringe barrel to prevent contamination of the fluid. The prior art includes hypodermic syringes that achieve this isolation with a barrier between the chamber and the needle cannula. These prior art hypodermic syringes may include a needle cannula with a proximally facing point for piercing the barrier and enabling fluid in the chamber to communicate with the needle cannula. Some prior art hypodermic syringes use the needle shield for moving the needle cannula in a proximal direction to pierce the barrier. Thus, a health care worker may urge a prior art needle shield in a proximal direction to cause the proximally facing point of the needle cannula to pierce the barrier in the syringe barrel.

One prior art hypodermic syringe with a needle shield that can initially move in an axial direction for piercing the barrier is shown in U.S. Pat. No. 4,639,250.

The above-described prior art requires a first action by a health care worker to pierce the barrier, followed by a separate and distinct action to remove the needle shield.

SUMMARY OF THE INVENTION

The subject invention is directed to an activation assembly for a hypodermic syringe which enables a single efficient motion for placing the needle cannula in communication with fluid in the syringe barrel and for separating a needle shield from the syringe barrel.

A hypodermic syringe in accordance with the subject invention includes a syringe barrel with a proximal end, a distal end and a cylindrical wall extending therebetween to define a fluid-receiving chamber. The distal end of the syringe barrel includes a passage leading to the chamber. However, a barrier prevents fluid in the chamber from flowing through the passage and out of the barrel.

The hypodermic syringe further includes a needle assembly which comprises a needle hub and a needle cannula with a proximally facing point. The hub and needle cannula are able to move in a proximal direction to pierce the barrier in the syringe barrel. A needle shield is mounted to the distal end of the syringe barrel for protectively shielding the needle cannula.

The activation assembly of the subject invention may include cam means for guiding the needle shield initially in a proximal direction and subsequently in a distal direction in response to a unidirectional rotation of the needle shield. The cam means may define an arrangement of cooperating cam pins and cam slots. For example, at least one cam pin may be defined on an inwardly facing surface of the needle shield, and may be engageable with at least one cam slot on the syringe barrel.

The cam slot may include a locked position for lockingly but releasably engaging the cam pin and thereby releasably locking the needle shield in a fixed position relative to the syringe barrel. The locked position of the slot may be configured to resist movement of the needle shield relative to the syringe barrel in order to prevent accidentally piercing the barrier and removing the needle shield.

The cam slot may extend generally helically in a proximal direction from the locked position to an activated position. The cam slot may then change direction to extend generally helically from the activated position to the distal end of the syringe barrel. With this configuration, rotation of the needle shield relative to the syringe barrel causes the cam pin to follow the cam slot initially in a proximal direction and then subsequently in a distal direction.

As noted above, the needle hub is axially moveable relative to the distal end of the syringe barrel. The needle hub also is engageable with the needle shield. Thus, the initial rotation and proximal movement of the needle shield caused by the cam pin following the cam slot generates a proximal movement of the needle hub sufficient for the proximal tip of the needle cannula to pierce the barrier in the syringe barrel. The continued rotation and distal movement of the needle shield caused by the cam pin following the cam slot enables separation of the needle shield from both the syringe barrel and the needle hub.

BRIEF DESCRIPTION OF THE DRAWINGS

FIG. 1 is an exploded perspective view of a hypodermic syringe assembly in accordance with the subject invention.

FIG. 2 is a side elevational view of the syringe barrel shown in FIG. 1;

DETAILED DESCRIPTION OF THE PREFERRED EMBODIMENT

Figure 3:
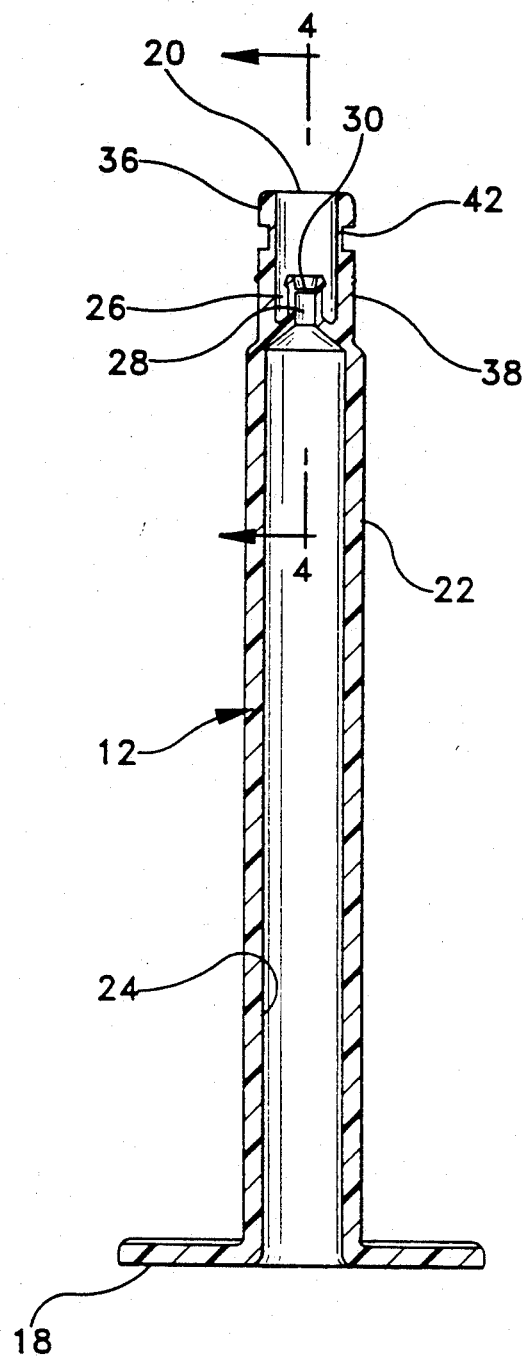
FIG. 3 is a cross-sectional view taken along line 3—3 in FIG. 2.

A hypodermic syringe in accordance with the subject invention is identified generally by the numeral 10 in FIGS. 1 and 10–12. Hypodermic syringe includes a syringe barrel 12, a needle assembly 14, and a needle shield 16.

As shown most clearly in FIGS. 1–4, syringe barrel 12 includes an open proximal end 18, a distal end 20 and a cylindrical wall 22 extending there between to define a fluid-receiving chamber 24. A plunger (not shown) can be slidingly disposed in fluid-tight engagement with the cylindrical wall 22 for urging fluid from chamber 24 as explained further herein.

Figure 4:
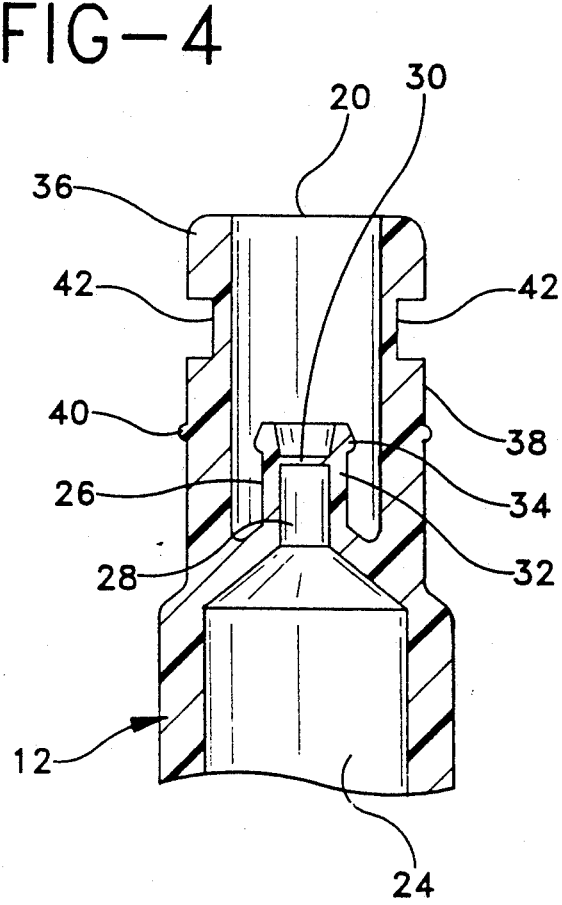
FIG. 4 is a cross-sectional view taken along line 4—4 in FIG. 3.
Figure 5:
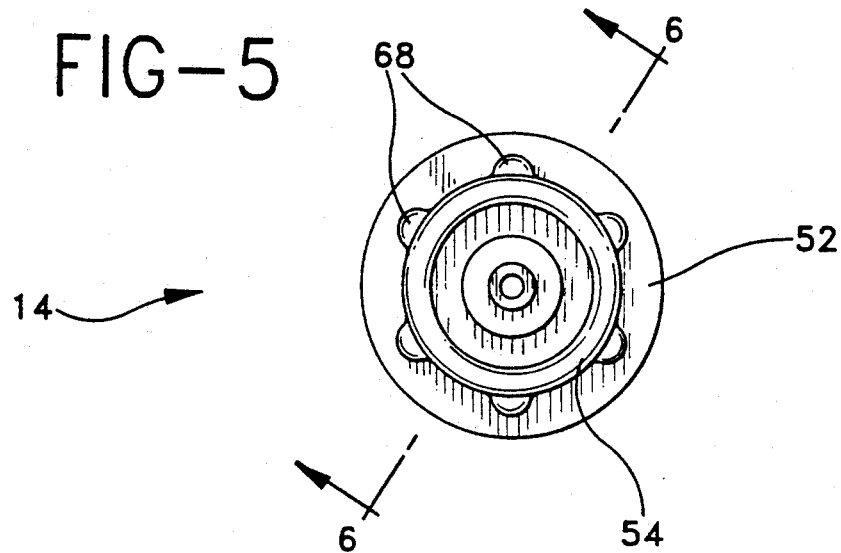
FIG. 5 is a bottom plan view of the needle hub shown in FIG. 1.
Figure 6:
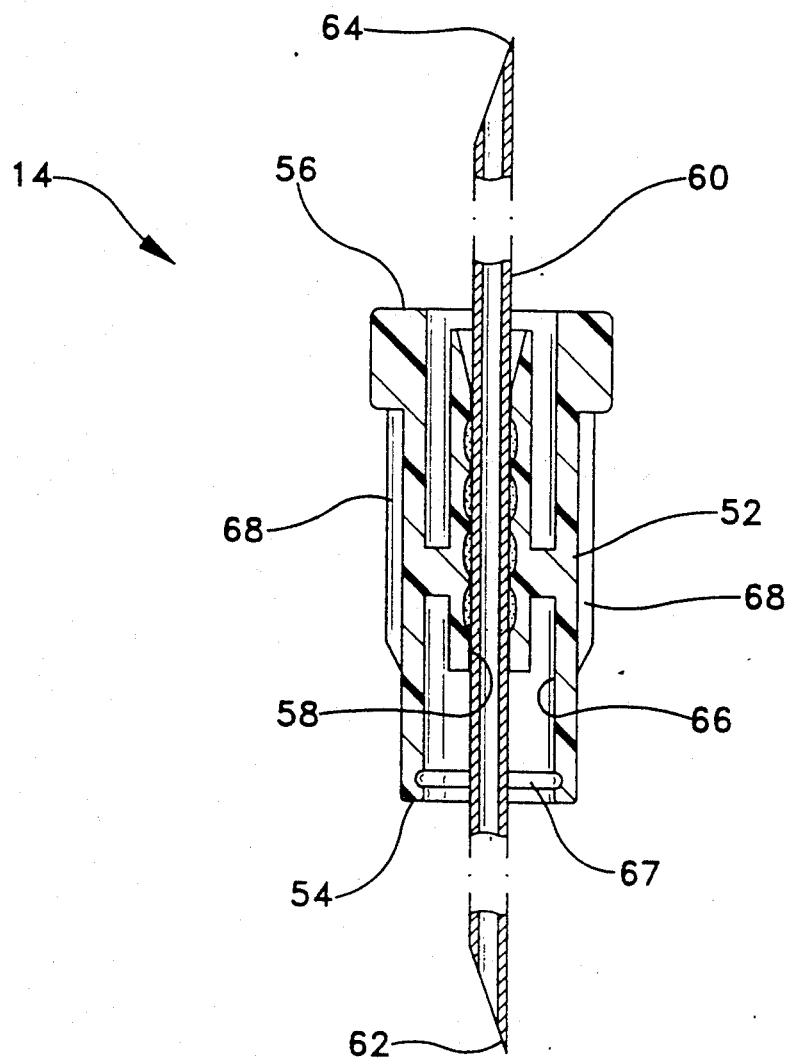
FIG. 6 is a cross-sectional view taken along line 6—6 in FIG. 5.

With reference to FIGS. 3 and 4, distal end 20 of syringe barrel 12 is characterized by a tip 26 having an axially extending passage 28 communicating with chamber 24. The passage, however, is characterized by a fluid impervious barrier 30 intermediate the length of tip 26. As depicted herein, barrier 30 is unitarily molded with syringe barrel 12 to define a suitable thickness. The barrier may also be formed as part of a separate component which is attached to the syringe barrel in the base position as barrier 30 in this embodiment. The barrier may be made of a variety of materials such as thermoplastic, thermoplastic elastomer, natural rubber, synthetic rubber or combinations thereof. It is preferred to have means for locating the needle hub in the collar in the position it will occupy before use of the syringe and to prevent the needle from contacting the barrier before the user decides to activate the syringe. This result can be accomplished by providing an interference or frictional fit between the needle hub and the syringe barrel and/or by providing specific structure to help position the hub in the collar. To this end tip 26 of syringe barrel 12 is further characterized by a generally cylindrical outer surface 32 having an annular rib 34 extending outwardly therefrom at a location intermediate the length of tip 26. Rib 34 helps define an initial mounting position of needle assembly 14 relative to syringe barrel 12, as explained in greater detail below.

The distal end of syringe barrel 12 is further characterized by a cylindrical collar 36 disposed in spaced concentric relationship around tip 26. Collar 36 includes an outer cylindrical surface 38 having outwardly extending annular engagement ribs 40 for providing an interference fit with needle shield 16 as explained further herein.

The outer surface of collar 36 is further characterized by a pair of opposed cam slots 42. As shown most clearly in FIGS. 1 and 2, each slot 42 is of generally V-shape, with a closed end 44 intermediate the axial length of collar 36. The closed end of cam slot 42 is characterized by a locking detent 46 for retaining the needle shield in a locked position and for helping to prevent unintended movement between needle shield 16 and syringe barrel 12. In this position, the needle shield cannot be removed from the barrel. Cam slot 42 includes an activation leg 47 which extends generally helically in a proximal direction from closed end 44 to an activated position 48. Activation leg 47 of cam slot 42 is aligned at an angle within the range of 50° to 70° to a plane passing through the longitudinal axis of syringe barrel 12 with an angle of approximately 60°.

Cam slot 42 further includes a shield removal leg 49 which continues from activated position 48 generally helically in a distal direction to an open end 50 at the extreme distal end of syringe barrel 12. Shield removal leg 49 of cam slot 42 defines a helix generated oppositely from the activation leg of cam slot 42. Thus, the cam slot defines a generally V-shape applied to cylindrical outer surface 38 of collar 36. However, in the preferred embodiment illustrated herein, shield removal leg 94 of cam slot 42 defines an angle of approximately 25° to a plane passing through the longitudinal axis of syringe barrel 12.

Needle assembly 14 includes a unitarily molded thermoplastic needle hub 52 having opposed proximal and distal ends 54 and 56 respectively and a needle receiving aperture 58 extending axially therethrough. A needle cannula 60 is rigidly fixed in aperture 58 by epoxy or other such means. Needle cannula 60 includes a proximally facing point 62 projecting beyond proximal end 54 of hub 52 and a distally facing point 64 projecting beyond distal end 56 of hub 52.

A generally cylindrical cavity 66 extends axially into proximal end 54 of hub 52. Cavity 66 defines an inside diameter slightly greater than the outside diameter of cylindrical outer surface 32 of tip 26 on syringe barrel 12. The inside diameter of cavity 66 includes circumferential groove 67 adapted to receive annular rib 34 on the outer cylindrical surface of tip 26 to position the needle hub.

Portions of hub 52 adjacent proximal end 54 define an outside diameter which is less than the inside diameter of collar 36 on syringe barrel 12. However, the outer surface of hub 52 includes a plurality of longitudinally extending ribs 68 at locations spaced from proximal end 54.

The relative dimensions of hub 14 and the tip and collar at distal end 20 of syringe barrel 12 enables hub 52 to be retained in an initial position on distal end of syringe barrel 12. More particularly, proximal end 54 of hub 52 can be telescoped into collar 36 until circumferential groove 67 in cavity 66 engages annular rib 34 extending around tip 26. The engagement of rib 34 with groove 67 prevents hub 52 from sliding distally out of its telescoped engagement with cylindrical collar 36. Simultaneously, the engagement of annular rib 34 on syringe tip 26 and groove 67 provides at least a temporary restraint against further telescoped advancement of hub 52 over syringe tip 26. This initial position of hub 52 on syringe barrel 12 places proximal tip 62 of needle cannula 60 a slight distance in the distal direction from barrier 30.

Figure 7:
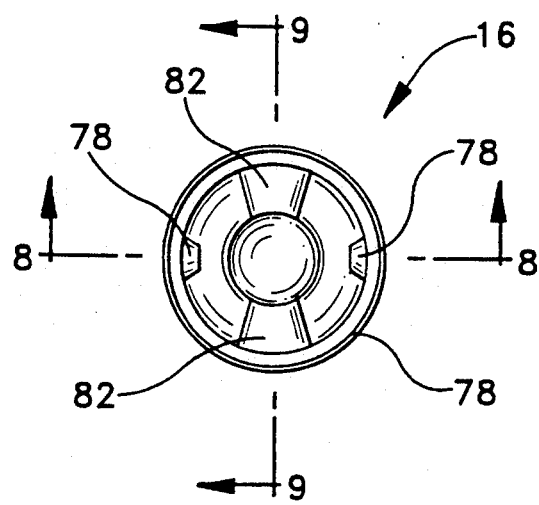
FIG. 7 is a bottom plan view of the needle shield shown in FIG. 1.
Figure 8:
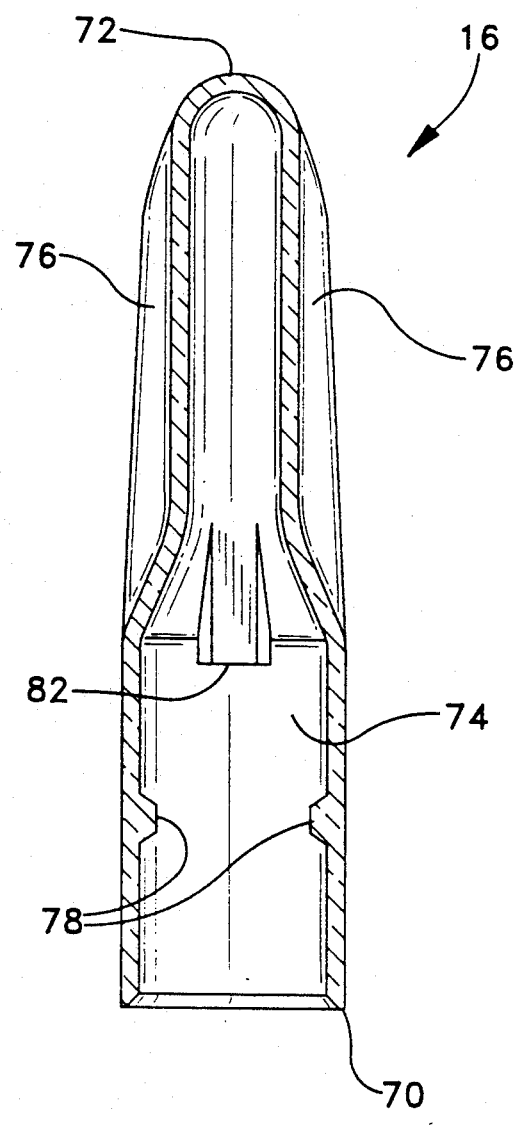
FIG. 8 is a cross-sectional view taken along line 8—8 in FIG. 7.
Figure 9:
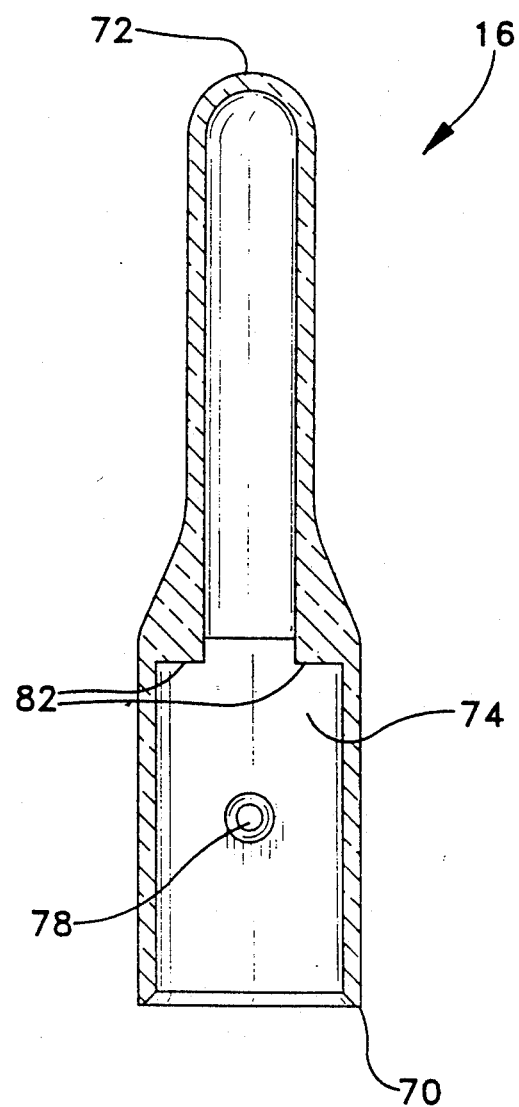
FIG. 9 is a cross-sectional view taken along line 9—9 in FIG. 7.

Needle shield 16, as shown most clearly in FIGS. 7–9, is unitarily molded from a rigid thermoplastic material and includes an open proximal end 70, a closed distal end 72 and a needle receiving chamber 74 therebetween. The outer surface of needle shield 16 is characterized by ribs 76 which facilitate gripping and rotation of shield 16, as explained further below.

Needle receiving cavity 74 of the needle shield includes a pair of opposed cam pins 78 extending radially inwardly and dimensioned to be received in cam slots 42 on the collar of syringe barrel 12. The cam pins may be generally frusto-conical or hemispherical protrusions formed during molding, after molding or as separate parts attached after molding or forming of the needle shield. Needle receiving cavity 74 of needle shield 16 is further characterized by a pair of opposed inwardly projecting stops 82 at locations intermediate cam pins 78 and distal end 72 of needle shield 16.

Figure 10:
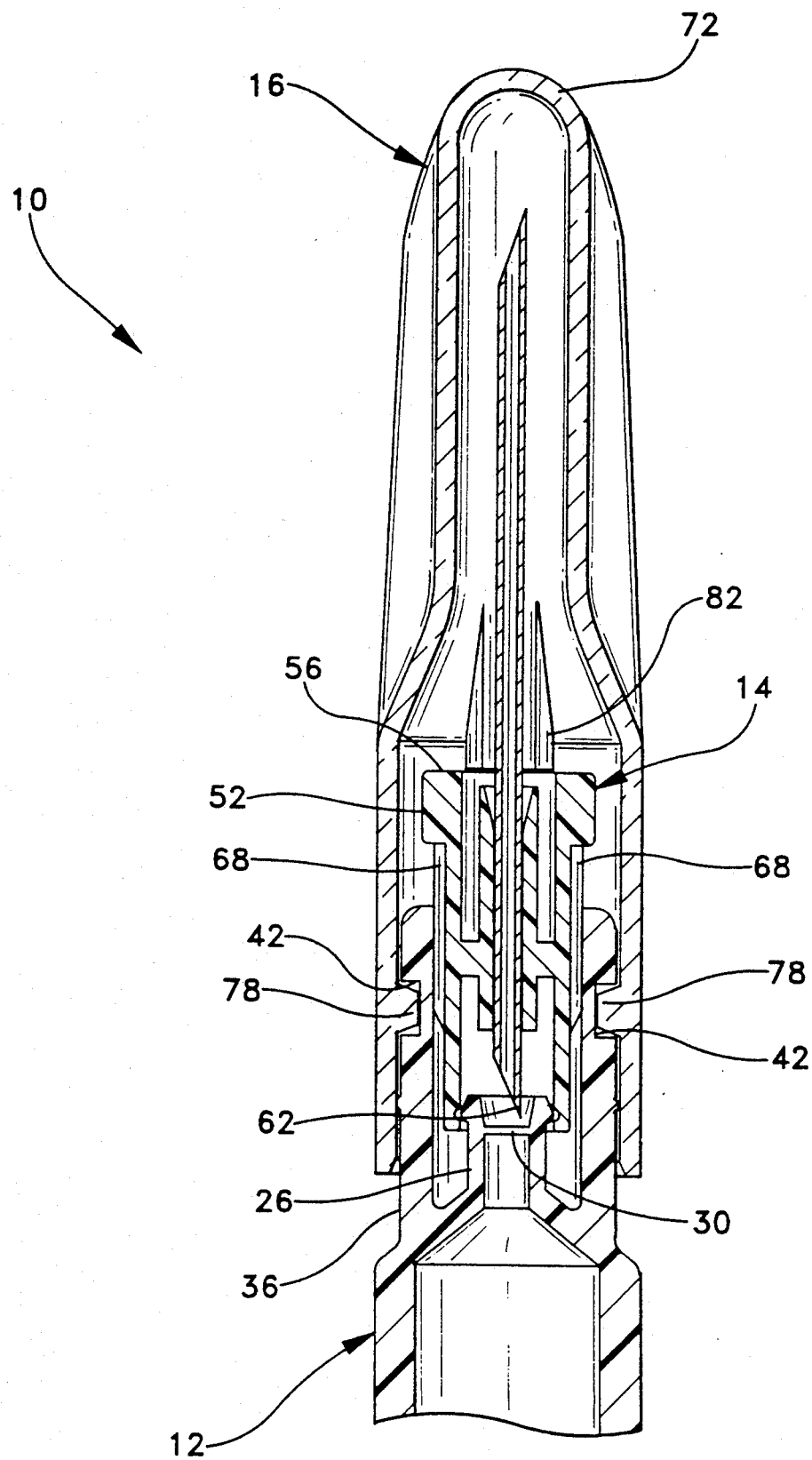
FIG. 10 is a cross-sectional view of the assembled hypodermic syringe prior to piercing the barrier in the syringe barrel.
Figure 11:
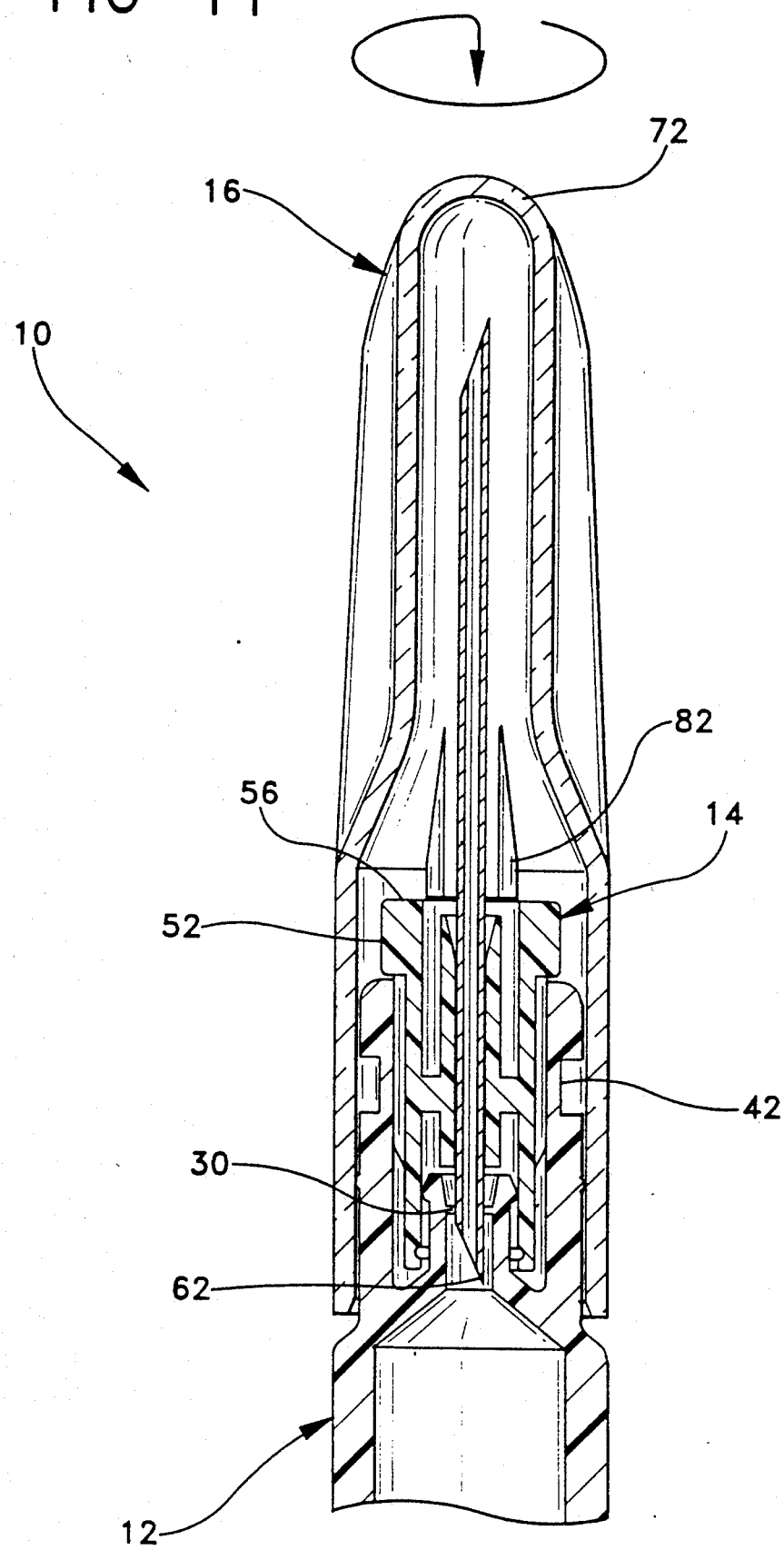
FIG. 11 is a cross-sectional view similar to FIG. 10, but showing the syringe barrier having been pierced.
Figure 12:
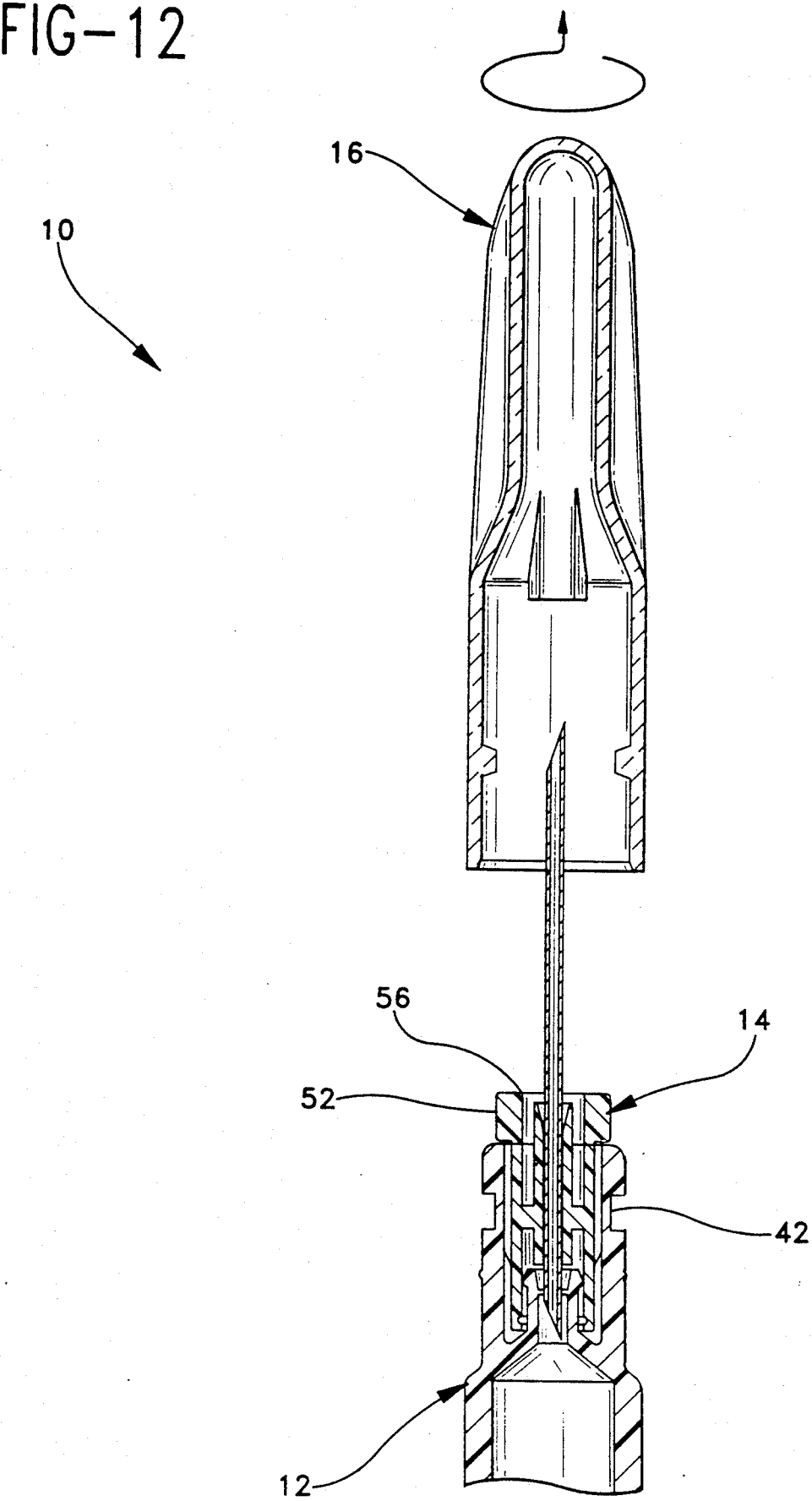
FIG. 12 is a cross-sectional view similar to FIGS. 10 and 11, but showing the needle shield being removed.

Hypodermic syringe 10 is assembled, as shown in FIG. 10, by telescoping proximal end 54 of the hub of needle assembly 14 into collar 36 and over tip 26 at the distal end of syringe barrel 12. This telescoped movement is terminated when proximal end 54 of hub 52 engages annular rib 34 on the outer circumferential surface of syringe tip 26. Separation of hub 52 from syringe barrel 12 in a distal direction is prevented by frictional engagement between longitudinal ribs 68 and cylindrical collar 36. Thus, needle assembly 14 is temporarily mounted in an axial position on syringe barrel 12 where proximal tip 62 of needle cannula 60 is spaced slightly in a distal direction from barrier 30 on syringe barrel 12.

Assembly of hypodermic syringe 10 proceeds, as shown in FIG. 10, by telescoping needle shield 16 over collar 36 until stops 82 of needle shield 16 engage distal end 56 of needle hub 52. Once this assembled position has been achieved, opposed locations on needle shield 16 that are aligned with closed ends 44 of cam slots 42 are staked inwardly to define cam pins 78. The cam pins are initially retained in closed ends 44 of cam slots 42 by the locking detents 46 in cam slots 42. The chamber of syringe barrel 12 may then be pre-filled with an appropriate solution to be injected and may be sealed by a plunger and piston combination or by other known means. The hypodermic syringe assembly will remain in this assembled and pre-filled condition until immediately prior to use.

Hypodermic syringe 10 is employed by rotating needle shield 16 relative to syringe barrel 12. These rotational forces cause cam pins 78 on needle shield 16 to follow cam slots 42 on the collar of syringe barrel 12. In particular, as shown most clearly in FIG. 11, the initial rotation of needle shield 16 relative to syringe barrel 12 will cause an axial movement of the needle shield in a proximal direction relative to syringe barrel 12. Stops 82 on needle shield 16 engage distal end 56 of needle hub 52 and cause needle assembly 14 to move proximally with needle shield 16. After sufficient cam-guided proximal movement of needle assembly 14 and needle shield 16, the proximal point of needle cannula 60 will pierce through barrier 30 to provide communication between needle cannula 60 and chamber 24 of the syringe barrel. The relatively large angle of activation leg 47 of cam slot 42 provides a desirable mechanical advantage for initially urging proximal end 54 of hub 52 over annular rib 34 on syringe tip 26 and continued mechanical advantage for urging the hub distally. Ribs 68 of hub 52 preferably define a diameter which is slightly less than the inner circumferential surface of collar 36 for helping to align the needle assembly with the longitudinal axis of the barrel and to prevent any cocking or binding of the hub with inside surfaces of the collar.

Continued rotational movement of needle shield 16 causes cam pins 78 to continue following cam slots 42 through shield removal legs 49 of the cam slots 42. In this position, needle shield 16 will be substantially separated from syringe barrel 12 and can be freely axially removed therefrom. It must be emphasized that this initial penetration of barrier 30, and the subsequent separation of needle shield 16 to place hypodermic syringe 10 in condition for use, is achieved by simple continuous rotational movement of needle shield 16 relative to syringe barrel 12. The above described configuration of cam slots 42 convert this continuous rotational movement into an initial proximal movement of needle shield 16 over syringe barrel 12 and a subsequent distal movement of needle shield 16 relative to syringe barrel 12.

It should also be noted that in this preferred embodiment the needle shield cannot be removed from the barrel until the rotational movement of the needle shield with respect to the barrel is complete and the barrier is penetrated by the needle. This means to prevent removal of the needle shield before syringe activation is an important feature of the preferred embodiment.

The embodiment described hereinabove requires rotation of the needle shield in a specific angular direction with respect to the cam path or slot. However, it is within the purview of this invention to include a dual or symmetrical cam path or paths to allow the barrier to be pierced by rotating the needle shield either in a clockwise direction or a counter-clockwise direction with respect to the barrel.

The preferred embodiment described hereinabove includes a cam path or slot described on the outer cylindrical surface of collar 36 of barrel 12, and a cam pin or follower 78 on the inside of the needle shield. It is also within the purview of this invention to include the cam path inside the needle shield and the cam pin or follower on the outside of the collar. In addition, it is also within the scope of this invention how the cam path on the inside of the barrel collar and the needle shield having cylindrical structure sized to fit within the collar and containing an outwardly directed cam follower or pin, or the reverse of this structure where the pin or cam follower projects inwardly from the collar and the needle shield contains an outwardly facing cam path which accepts the pin or follower.

What is claimed is:

1. A hypodermic syringe having a syringe barrel with opposed proximal and distal ends and a fluid-receiving chamber therebetween, a passage extending through said distal end for communication with said chamber, and a pierceable barrier for blocking fluid flow through said passage, a needle cannula mounted to said distal end of said syringe barrel and being selectively movable in a proximal direction for piercing said barrier, a needle shield mounted to said syringe barrel for covering said needle cannula, said syringe including an activation assembly comprising:

first and second cooperating cam means disposed respectively on said syringe barrel and said needle shield, said cam means being responsive to unidirectional rotation of said needle shield relative to said syringe barrel for initially moving said needle shield and said needle cannula in said proximal direction sufficiently for piercing said barrier and for subsequently moving said needle shield in a distal direction for separating said needle shield from said syringe barrel.

2. The syringe of claim 1, wherein said first cam means is a cam slot on a selected one of said syringe barrel and said needle shield, and wherein said second cam means is a cam pin on a selected other of said syringe barrel of said needle shield dimensioned for slidable engagement in said cam slot.

3. The syringe of claim 2, wherein said cam slot is disposed on said syringe barrel and wherein said cam pin is disposed on said needle shield.

4. The syringe of claim 3, wherein said cam slot includes an activation leg extending generally helically in a proximal direction from a closed end to an activated position, and a shield removal leg extending generally helically from said activated position to said distal end of said syringe barrel.

5. The syringe of claim 4, wherein said closed end of said cam slot includes a locking detent for preventing axial movement of said needle shield relative to said syringe barrel in response to axial forces exerted thereon.

6. The syringe of claim 4, wherein said syringe barrel is generally cylindrical and includes a longitudinal axis, said activation leg of said cam slot being aligned to a plane through said longitudinal axis at an angle in the range of about 50° to 70° for achieving efficient mechanical advantage for piercing said barrier.

7. The syringe of claim 6, wherein said shield removal leg of said cam slot is aligned to said plane at an angle less than said activation leg for achieving efficient separation of said needle shield from said syringe barrel.

8. The syringe of claim 2, wherein said cam pin is defined by an inwardly formed protrusion on said needle shield.

9. The syringe of claim 1 further comprising an inwardly extending stop on said needle shield for urging said needle cannula in a proximal direction for piercing said barrier.

10. The syringe of claim 1 further comprising means for preventing distal movement of said needle cannula after piercing said barrier, such that said needle cannula remains fixedly mounted to said syringe barrel after removal of said needle shield.

11. The syringe of claim 1 further comprising means for preventing removal of said needle shield before said cannula is moved proximally to pierce said barrier.

12. The syringe of claim 1 wherein said barrier is made of material selected from the group consisting of thermoplastic, thermoplastic elastomers, natural rubber, synthetic rubber or combinations thereof.

13. A hypodermic syringe comprising:
a syringe barrel with opposed proximal and distal ends and a fluid-receiving chamber therebetween, as passage extending through said distal end for communication with said chamber and a pierceable barrier blocking fluid flow through said passage;
a needle hub mounted to said distal end of said syringe barrel external of said barrier and being selectively moveable in a proximal direction;
a needle cannula fixedly mounted to said needle hub for movement therewith and having a proximally facing point aligned with said barrier for piercing said barrier in response to said proximal movement of said hub;
a needle shield rotatably and axially moveable on said distal end of said syringe barrel for protectively covering said needle cannula; and
first and second cam means disposed respectively on said syringe barrel and said needle shield, said cam means being configured such that continuous rotation of said needle shield relative to said syringe barrel generates an initial movement of said needle shield in a proximal direction for urging said hub and said needle cannula proximally a sufficient distance for piercing said barrier and for subsequently generating movement of said needle shield in a distal direction in response to said continuous rotation for separating said needle shield from said syringe barrel.

14. The hypodermic syringe of claim 13, wherein said needle shield includes a proximally facing surface engageable with said needle hub for urging said needle hub and said needle cannula in a proximal direction for piercing said barrier.

15. The hypodermic syringe of claim 13, wherein said first cam means comprises at least one cam slot and wherein said second cam means comprises at least one cam pin dimensioned for following said cam slot.

16. The hypodermic syringe of claim 15, wherein said cam slot is disposed on said syringe barrel and wherein said cam pin is disposed on said needle shield.

17. The hypodermic syringe of claim 16, wherein said cam slot includes a first leg extending from a start position generally helically in a proximal direction to an activated position and a second leg extending generally helically from said activated position in a distal direction to said distal end of said syringe barrel.

18. The hypodermic syringe of claim 16, wherein said syringe barrel includes a tip at said distal end through which said passage extends and a collar surrounding said tip, said cam slot being disposed on an outwardly facing surface of said collar, said needle hub being dimensioned for telescoped insertion intermediate said tip and said collar and being dimensioned for frictional engagement therebetween for retaining said hub and said needle cannula on said syringe barrel after separation of said needle shield therefrom.

19. A hypodermic syringe comprising:
a syringe barrel with opposed proximal and distal ends and a fluid-receiving chamber therebetween a tip disposed at said distal end and having a passage therethrough for communication with said chamber, a pierceable barrier in said syringe barrel for blocking fluid flow through said passage, a generally cylindrical collar disposed around said tip in spaced concentric relationship thereto, said collar having an outer surface with at least one cam slot formed therein, said cam slot extending from a start position spaced generally helically in a proximal direction from said distal end to an activated position and extending from said activated position generally helically to said distal end of said syringe barrel;
a needle hub mounted for sliding telescoped movement within said cylindrical collar;
a needle cannula fixedly mounted to said needle hub and disposed external of said barrier, said needle cannula including a proximally facing point aligned for piercing said barrier in response to said proximal movement of said hub; and
a needle shield mounted to said collar for axial and rotational movement thereon, said needle shield being configured for protectively enclosing said needle cannula, said needle shield comprising an inner surface having at least one cam pin formed thereon for sliding cam-guided movement in said cam slot of said collar and a proximally facing surface for engagement with said needle hub, whereby rotation of said needle shield relative to said syringe barrel causes said cam pin to follow said cam slot and initially urges said needle shield and said needle hub in said proximal direction such that said needle cannula pierces said barrier and subsequently urges said needle shield in a distal direction for removal of said needle shield from said syringe barrel.

* * * * *